United States Patent [19]
Forester et al.

[11] Patent Number: 5,823,677
[45] Date of Patent: Oct. 20, 1998

[54] METHOD OF IDENTIFYING A SUBSTANCE BY INFRARED IMAGING

[75] Inventors: William K. Forester, Kalamazoo; Timothy J. Lobbes, Menominee, both of Mich.

[73] Assignee: The Board of Trustees of Western Michigan, Kalamazoo, Mich.

[21] Appl. No.: 617,044

[22] Filed: Mar. 18, 1996

[51] Int. Cl.$^6$ .......................... G01N 25/00; G01N 25/18
[52] U.S. Cl. ................. 374/10; 374/11; 374/45; 250/341.6
[58] Field of Search ................. 374/10, 11, 45; 250/341.6

[56] References Cited

U.S. PATENT DOCUMENTS

| | | | |
|---|---|---|---|
| 2,705,417 | 4/1955 | Romo et al. | 374/10 |
| 3,271,996 | 9/1966 | Paulik et al. | 374/10 |
| 3,498,113 | 3/1970 | Whatley | 374/10 |
| 3,726,126 | 4/1973 | De Vittorio | 374/10 |
| 3,747,755 | 7/1973 | Senturia et al. . | |
| 3,981,175 | 9/1976 | Hammond, III et al. | 374/10 |
| 4,306,151 | 12/1981 | Chase . | |
| 4,364,675 | 12/1982 | Frushour | 374/10 |
| 4,507,556 | 3/1985 | Brenholdt . | |
| 4,567,849 | 2/1986 | Wan | 374/11 |
| 4,840,706 | 6/1989 | Campbell . | |
| 4,928,254 | 5/1990 | Knudsen et al. | 374/10 |
| 4,935,628 | 6/1990 | Martin et al. . | |
| 4,965,452 | 10/1990 | Sturm . | |
| 5,134,291 | 7/1992 | Ruhl, Jr. et al. . | |
| 5,278,411 | 1/1994 | Popil et al. . | |
| 5,346,306 | 9/1994 | Reading et al. | 374/10 |
| 5,364,502 | 11/1994 | LeClerc et al. . | |
| 5,378,320 | 1/1995 | LeClerc et al. . | |
| 5,489,778 | 2/1996 | Burmester et al. | 250/341.6 |
| 5,646,405 | 7/1997 | Nevel et al. | 250/341.6 |
| 5,672,289 | 9/1997 | O'Neill | 374/11 |

OTHER PUBLICATIONS

Muller, R. H, "Differential Thermal Analysis," Analytical Chemistry, vol. 35, No. 4 (Apr. 1963).

Chiu, J., "Identification of Organic Compounds by Differential Thermal Dynamic Analysis," Analytical Chemistry vol. 34, No. 13 (Dec. 1962).

Murphy, C.B., "Differential Thermal Analysis," Analytical Chemistry, vol. 30, No. 4 (Apr. 1958).

*Primary Examiner*—Diego F.F. Gutierrez
*Attorney, Agent, or Firm*—Flynn, Thiel, Boutell & Tanis, P.C.

[57] ABSTRACT

The method of detecting and identifying a substance in a sample requires the sample to be changed from a first temperature to a second temperature, the sample scanned with an instrument for measuring infrared radiation, the temperature difference between the temperature of the substance and a reference temperature determined, and the substance identified based on this temperature difference. The infrared method allows for the objective determination of a substance in a sample without the necessity of the labor and time required in conventional methods and is especially suitable for detecting the presence of "stickies" in recycled paper.

10 Claims, No Drawings

5,823,677

METHOD OF IDENTIFYING A SUBSTANCE BY INFRARED IMAGING

FIELD OF THE INVENTION

The invention relates to methods of detecting and identifying substances contained in a sample and, more specifically, to a method of identifying "stickies" contained in recycled paper.

DESCRIPTION OF THE PRIOR ART

The use of infrared radiation to measure process conditions during paper manufacture is well known. For example, Brenholdt, U.S. Pat. No. 4,507,556, discloses the use of infrared radiation in determining the consistency of a pulp stock. Campbell, U.S. Pat. No. 4,840,706, shows the use of an infra-red scanning gauge to measure the moisture content of a paper-web during a paper making process. LeClerc et al, U.S. Pat. Nos. 5,364,502 and 5,378,320, show the use of infrared spectrophotometry to analyze alkali concentrations in pulping liquors used during manufacture of kraft pulp.

Ruhl, Jr. et al, U.S. Pat. No. 5,134,291, shows infrared radiation being used to sort plastic containers made of different types of polymers. It is also known to use infrared radiation to detect and measure the amount of a contaminate present in a sample. Senturia et al, U.S. Pat. No. 3,747,755, shows the use of diffuse and specular reflection of infrared radiation from the sample to classify that sample into different components, such as paper and plastics. Chase, U.S. Pat. No. 4,306,151, shows the use of infrared radiation to measure the amount of substance associated with a material in the presence of a contaminate, and more specifically, to a method for measuring the amount of water associated with a paper material in the presence of carbon. Martin et al, U.S. Pat. No. 4,935,628, and Popil et al, U.S. Pat. No. 5,278,411, both disclose the use of infrared radiation in detecting the presence of ink in paper, and Sturm, U.S. Pat. No. 4,965,452, shows the use of infrared radiation to determine the quality of a kaolinite clay coating on paper.

Although, as the methods as discussed above illustrate, the use of infrared radiation has become fairly widespread in the control and analysis of various parameters during paper manufacture, there is no satisfactory method of analyzing recycled paper for the presence of thermoplastic contaminates, commonly known as "stickies", in converting operations in the paper industry. Current methods of "stickies" detection are the Berol Method, Sulzer Escher Weiss Method, Fluorescent Speck Counting Method, Southeast Paper Contaminant Content Method, Peel Test, Hotmelt Staining Test and Abatibi Price Speck Count Method. Although all of these methods differ in their method of determining the amount of "stickies" contained in a paper sample, all of these methods are expensive, very time consuming, require a skilled technician to perform the analysis and require a certain degree of subjectivity. Therefore, there is a need for a method of detecting contaminates in a sample, more particularly, stickies in a paper sample, which does not require specifically trained personnel, is inexpensive and completely objective. The present invention addresses this need.

SUMMARY OF THE INVENTION

A first embodiment of the present invention is directed to a method of detecting and identifying a substance contained in a sample which also contains a reference material comprising the steps of providing said sample at a first temperature; allowing said sample to change from said first temperature to a second temperature; scanning the sample with a means for measuring infrared radiation; determining the temperature difference between said substance and said reference material; and identifying said substance by the temperature difference between the substance and the reference material.

A second embodiment of the present invention is directed to a method of detecting and identifying a substance contained in a sample comprising the steps of providing a sample at a first temperature; allowing the sample to change from said first temperature to a second temperature; scanning the sample with a means for measuring infrared radiation; determining the temperature difference between the substance and the ambient temperature; and identifying said substance by the temperature difference between the substance and the ambient temperature.

In the first embodiment of the present invention, the known temperature is the temperature of reference material contained in the sample and, in the second embodiment of the present invention, the known temperature is the ambient temperature. Since all materials have a characteristic rate of cooling or warming at a particular ambient temperature, the difference in temperature between an unknown substance and a reference material which has been allowed to cool or warm for a controlled period of time at an ambient temperature can be used to identify the unknown substance. Additionally, the temperature of an unknown substance after it has been allowed to cool or warm for a controlled period of time at the ambient temperature can also be used to identify the substance based on its peculiar thermal properties.

DETAILED DESCRIPTION OF THE PREFERRED EMBODIMENTS

It is known that each substance has characteristic thermal properties. The combination of heat capacity and thermal conductivity gives each substance an unique rate of warming and thermal dissipation, cooling, which will result in a characteristic surface temperature for each substance when allowed to warm or cool for a controlled period of time at an ambient temperature. Because substances warm and cool at different rates, their surface temperature will be different at any given point in time. There is an inverse relationship between thermal conductivity and thermal resistance, R value, for a substance. As such, substances having a high thermal conductivity will tend to have a higher surface temperature after being allowed to cool or a lower surface temperature after being allowed to warm for a given period of time than the surface of a substance with a low thermal conductivity.

R value or thermal resistance is a measure of a material's ability to restrict heat transfer. Estimated R values are given in FIG. 7.

R=L/K

R=Thermal Resistance Value

L=Material Thickness

K=Thermal Conductivity

The R value of a material is a characterization based on the thickness of the material. This value will increase with an increase in material thickness. Air entrainment also will increase the R value. This is evident with the calculated R value of cellulose. The calculated value is very low, but with air entrainment, the actual R value is much higher.

The smaller the thermal conductivity the greater the thermal resistance for a given thickness of material. The thermal resistance will cause a temperature difference which will allow for the characterization of stickies by infrared detection by measuring the rate of heat loss from a constant initial temperature.

The characterization of overall thermal performance requires knowledge of the average surface temperature and the average air to surface temperature difference. Thermographic inspection can establish the surface temperature sufficiently to characterize the thermal performance without knowledge of the actual R value. This thermal performance is known as "Temperature Index" or T.I. and is calculated according to the following formula. In this experiment, the T.I. will be used to categorize the stickies.

T.I.=[To−Ta]/Ta, wherein

T.I.=Temperature Index

To=Temperature Stickie, C

Ta=Temperature Ambient, C

Thermal conductivity is the measure of a substance's ability to transmit heat energy. Different thermal images, generated by the thermographic camera, are the result of the different thermal conductivity values associated with different chemical compounds. A substance with a high thermal conductivity value will transmit larger amounts of heat per unit time. This heat will be transmitted at a shorter wavelength radiation. This heat will register with the thermographic camera as a hot spot and be visually represented as a yellow or white region. The Agema 470 thermographic camera, used for this project, allows for the measurement of a desired temperature span. As an object approaches the upper limit of the temperature span, the object will appear yellow, while an object approaching the lower limit of the temperature span will appear blue. Any parts of an object that exceed the upper limit will appear white and those that exceed the lower limit will appear black.

To achieve images with proper temperature profiles, the camera must be calibrated correctly. This calibration factor is known as emissivity. Emissivity is defined as the ratio of the amount of radiant energy the measured object emits to that emitted by a perfect radiator at the same temperature. A perfect radiator, known as a "black body," has an emissivity of 1.0. It has been experimentally determined that different substances have differing emissivity values. In this example, the emissivity will be determined by using a thermocouple to measure the surface temperature of the stickie. The emissivity of the camera will be manipulated so that the camera temperature matches the thermocouple temperature.

The thermographic camera gives a visual representation of surface temperature across the entire handsheet. The yellow/white regions will be areas of high surface temperature relative to the temperature scale. The darker regions will be areas of low surface temperature. As the sample is allowed to cool or warm, the difference between the surface temperature and ambient temperature will approach zero. As substances cool or warm at different rates, their surface temperature will be different at any given time. This characteristic cooling or warming rate can be used to identify different materials.

EXAMPLE

The main variable of this example that will be measured is the temperature difference between a stickie and the cellulose of a blotter sheet. Other variables to be noted are the emissivity, measurable temperature span, and the ambient temperature. The ambient temperature will affect the rate of heat loss between the cellulose, stickie, and the atmosphere. The type of stickies to be used are polystyrene, polypropylene, and polyester. These stickies were chosen because they are representative of the main contaminants found in recycle furnish.

These stickies and cellulose have varying thermal conductivity values. They are as follows:

| TYPE | Thermal Conductivity ($10^{-4}$ cal/cm s C) |
|---|---|
| Polyester | 6–10 |
| Polystyrene | 3–4 |
| Polypropylene | 2–3 |
| Cellulose | 2 | wherein cal=calories, cm=centimeters in depth, s=seconds, and

C=degrees Celsius

According to these values, a temperature gradient will exist between all stickies and the cellulose blotter sheet. Also, a characteristic gradient will exist for each stickie, when allowed to lose heat for the same amount of time. These characteristic gradients will allow for the identification of the type of stickie by the surface temperature. This gradient is a function of the rate of heat loss that is uniquely associated with each type of stickie.

The procedure for producing a thermal image is as follows:

1. A plurality of blotter sheets, each containing one type of stickie and one blotter sheet containing a composite sample of all stickies, were produced.

2. All blotter sheets were heated to 105 C.

3. The composite blotter sheets were removed and viewed under the thermographic camera to determine the time, post oven, that provided the best clarity. This time (post oven) will be the time the sheets are allowed to cool before capturing the image.

4. The composite sheets were placed back into the oven.

5. A sheet with a singular type of stickie was removed from the oven and placed under the camera. At the predetermined post oven time, the image was captured with the thermographic camera.

6. Step 5 was repeated for all the remaining blotter sheets having a singular type of stickie.

7. The images were analyzed for surface temperature using IRwin thermal image analysis software.

These images were used to differentiate between stickies and cellulose, and also between stickies themselves.

Each sample was removed from the 105 C. oven and allowed to cool for 45 seconds at the same ambient room temperature of 23 C. After the 45 seconds, the image was captured. The images, upon exiting the oven, appeared white hot and the constituents in the sheet gradually lost heat but not at the same rate. This heat loss is due to the thermal conductivity of the constituents. The cellulose of the handsheet medium lost heat at the same rate in all the tests. This is shown by the similar base sheet temperatures as shown in Tables 1–4 as SPO4.

As shown in Table 3, the polyester sample had the highest surface temperature, after 45 seconds, and also had the highest thermal conductivity of $5 \times 10^{-4}$ cal/cm s C. This is a result of the low R value of polyester. Polyester allows heat transfer better than cellulose and thus has a higher surface temperature.

The thermographic analysis of polypropylene is presented in Table 1. It is evident from the thermographic analysis that the temperature differential between cellulose and polypropylene is relatively low. This is explained by the high R value of polypropylene and the higher R value of cellulose. The high R value restricts the heat flow from the interior of the stickie to the surface. This results in a low average surface temperature differential of 1.5 C.

Table 2 shows the analysis of polystyrene in relation to cellulose. This analysis shows that the average surface temperature differential between polystyrene and cellulose is 3.8 C. This results from the lower R value of polystyrene in relation to polypropylene.

Table 3 shows the analysis of polyester in relation to cellulose. This analysis shows that the average surface temperature differential between polyester and cellulose is 12.3 C. This is the result of polyester having the lowest R value of all three stickies tested.

Table 4 is a thermographic analysis of all three thermoplastics in relation to cellulose. This shows that the same differential surface temperature of each polymer in the composite sample is of the same magnitude as in the singular samples. A comparison of this is graphically represented in FIG. 1. From this data, I am able to differentiate, from the image, between the different type of stickies present. Further classification in Table 5 shows that differentiation is also possible by Temperature Index.

TABLE 1

POLYPROPYLENE

| | Temp. (°C.) | |
|---|---|---|
| SP01 | 32.1 | |
| SP02 | 31.6 | |
| SP03 | 31.2 | |
| SP04 | 30.1 | |
| | Difference | Formula |
| D101 | −1.4 | SP04–SP02 |
| D102 | −1.0 | SP04–SP03 |
| D103 | −2.0 | SP04–SP01 |

TABLE 2

POLYSTYRENE

| | Temp. (°C.) | |
|---|---|---|
| SP01 | 34.5 | |
| SP02 | 34.8 | |
| SP03 | 33.3 | |
| SP04 | 30.4 | |
| | Difference | Formula |
| D101 | −4.3 | SP04–SP02 |
| D102 | −2.9 | SP04–SP03 |
| D103 | −4.1 | SP04–SP01 |

TABLE 3

POLYESTER

| | Temp. (°C.) | |
|---|---|---|
| SP01 | 42.2 | |
| SP02 | 46.2 | |
| SP03 | 42.8 | |
| SP04 | 31.5 | |

TABLE 3-continued

POLYESTER

| | Difference | Formula |
|---|---|---|
| D101 | −14.7 | SP04–SP02 |
| D102 | −11.3 | SP04–SP03 |
| D103 | −10.8 | SP04–SP01 |

TABLE 4

COMPOSITE

| | Temp. (°C.) | |
|---|---|---|
| SP01 | 46.0 | |
| SP02 | 34.2 | |
| SP03 | 31.8 | |
| SP04 | 30.4 | |
| | Difference | Formula |
| D101 | −3.7 | SP04–SP02 |
| D102 | −1.4 | SP04–SP03 |
| D103 | −15.6 | SP04–SP01 |

TABLE 5

| TEMPERATURE DIFFERENTIAL °C. | POLYESTER | POLYSTYRENE | POLYPROPYLENE |
|---|---|---|---|
| | −14.7 | −4.3 | −1.4 |
| | −11.3 | −2.9 | −1.0 |
| | −10.8 | −4.1 | −2.0 |
| AVERAGE | 12.3 | 3.8 | 1.5 |
| COMPOSITE | 15.6 | 3.7 | 1.4 |
| TEMPERATURE INDEX | | | |
| AVERAGE | 0.7083 | 0.3359 | 0.2357 |
| COMPOSITE | 0.7969 | 0.3359 | 0.2422 |

While the invention has been described according to the preferred embodiment, it is clear that numerous modifications can be made without departing from the spirit and scope of the invention. The present invention can be used to detect and identify other substances contained in different sample mediums and is not merely limited to the identification of stickies in a cellulose-containing sample. Additionally, as discussed earlier, the present invention also covers the detection and identification of a substance contained in a sample by cooling the sample and allowing the sample to warm to determine the characteristic warming rate of the substance. Thus, the above description is not intended to restrict the scope of the invention beyond that defined by the following claims and their equivalents.

The embodiments of the invention in which an exclusive property or privilege is claimed are defined as follows:

1. A method of detecting and identifying at least one substance contained in a sample which also contains a reference material comprising the steps of providing said sample at a first temperature; allowing said sample to change from said first temperature to a second temperature; scanning the sample with a means for measuring infrared radiation after said sample has reached said second temperature so as to sense the temperature of said at least one substance and of said reference material; determining the temperature difference between said at least one substance and said reference material; and identifying said at least one substance by the temperature difference between said at least one substance and the reference material.

2. The method of claim 1, wherein said sample is heated to said first temperature and allowed to cool to said second temperature.

3. The method of claim 1, wherein the temperature difference is determined by measuring the temperature of the at least one substance and the reference material after the sample has been allowed to cool.

4. The method of claim 1, wherein the sample contains a plurality of different substances.

5. The method of claim 1, wherein the reference material is cellulose.

6. The method of claim 1, wherein the at least one substance is a thermoplastic material.

7. The method of claim 6, wherein the thermoplastic material is at least one member selected from the group consisting of a polyester, polystyrene and polypropylene.

8. The method of claim 7, wherein the means for measuring infrared radiation is a thermographic camera.

9. The method of claim 1, wherein said sample is cooled to said first temperature and allowed to warm to said second temperature.

10. The method of claim 1, wherein the temperature difference is determined by measuring the temperature of the at least one substance and the reference material after the at least one substance has been allowed to warm.

* * * * *

UNITED STATES PATENT AND TRADEMARK OFFICE
CERTIFICATE OF CORRECTION

PATENT NO. : 5 823 677
DATED : October 20, 1998
INVENTOR(S) : William K. FORESTER et al It is certified that error appears in the above-identified patent and that said Letters Patent is hereby corrected as shown below:

On the title page:

please change [73] Assignee: from
"The Board of Trustees of Western Michigan" to
---The Board of Trustees of Western Michigan University---.

Signed and Sealed this

Twenty-seventh Day of April, 1999

Attest:

Q. TODD DICKINSON

*Attesting Officer*  *Acting Commissioner of Patents and Trademarks*